United States Patent [19]
Griswold et al.

[11] Patent Number: 5,824,696
[45] Date of Patent: Oct. 20, 1998

[54] MEDICAMENTS

[75] Inventors: Don Edgar Griswold, North Wales, Pa.; John Wharton, London, United Kingdom

[73] Assignee: SmithKline Beecham Corporation, Philadelphia, Pa.

[21] Appl. No.: 115,968

[22] Filed: Sep. 1, 1993

[51] Int. Cl.$^6$ .......................... A61K 31/41; A61K 31/415
[52] U.S. Cl. .......................... 514/382; 514/303; 514/312; 514/381; 514/397
[58] Field of Search ..................................... 514/410, 397, 514/382, 303, 312, 381

[56] References Cited

U.S. PATENT DOCUMENTS 5,212,195  5/1993  Clark et al. ............................. 514/381

FOREIGN PATENT DOCUMENTS 9315047  8/1993  WIPO .

OTHER PUBLICATIONS

Caspritz, Arzneimittel forschung (1986), 36(11), 1605–8 Search Report.

Traficante, Arthritis Rheum. (1985) 28(4) 480 Search Report.

Jaffe, Arthritis Rheum. (1984) 27(7) 840 Search Report.

*Primary Examiner*—Robert Gerstl
*Attorney, Agent, or Firm*—Dara L. Dinner; Stephen Venetianer

[57] ABSTRACT

The present invention relates to the use of an angiotensin II receptor antagonist in the manufacture of a medicament for the treatment of chronic inflammatory disease states.

11 Claims, 1 Drawing Sheet

MEDICAMENTS

FIELD OF THE INVENTION

The present invention relates to angiotensin II (AII) receptor antagonists useful in the treatment of inflammatory conditions of the joint.

BACKGROUND OF THE INVENTION

Angiotensin II (referred to as AII hereinafter) is an octopeptide produced by enzymatic cleavage of angiotensin I by angiotensin converting enzyme (ACE). In peripheral tissues AII is a potent vasoconstrictor and has been implicated in vascular intimal hyperplasia and stenosis following endothelial damage (Laporte & Escher, *Biochem. Biophys. Res. Commun.*, Vol. 187, pp 1510–1516 (1992); and Azuma et al., *Br. J. Pharmacol.*, Vol. 106, pp 665–671 (1992)). In addition, AII stimulates angiogenesis in some animal models (Fernandez et al., *J. Lab. Clin. Med.*, Vol. 105, pp 141–145 (1985), Le Noble et al., *Eur. H. Pharmacol.*, Vol. 195, pp 305–306 (1991)); and induces expression of growth factors by vascular smooth muscle (Naftilan et al., *J. Clin. Invest.*, Vol. 83, pp 1419–1424 (1989) and may itself regulate proliferation of some cell types (Araki et al., *Biochem. Biophys. Res. Commun.*, Vol., 168, pp 350–357 (1990).

Rheumatoid arthritis, has been characterised by chronic synovial hypoxia, indicative of synovial hypoperfusion (Levick J. R., *J. Rheumatol.*, Vol. 17, pp 579–582 (1990), Stevens et al., *Arthritis Rheum.*, Vol. 34, pp 1508–1513 (1991)), and by synovial proliferation.

There remains a need for treatment of chronic inflammatory conditions by compounds which are capable of inhibiting the pathogenesis of arthritis and other diseases wherein the synovium is involved.

SUMMARY OF THE INVENTION

The present invention provides for a new method of treating chronic inflammatory conditions, such as arthritis, in a mammal, especially a human, which comprises administering to a subject in need thereof an effective non-toxic amount of an angiotensin II receptor antagonist.

The present invention also provides for the use of an angiotensin II receptor antagonist in the manufacture of a medicament for the treatment of chronic inflammatory conditions, such as arthritis, in a mammal, especially a human.

DETAILED DESCRIPTION OF THE FIGURES

Figure 1:
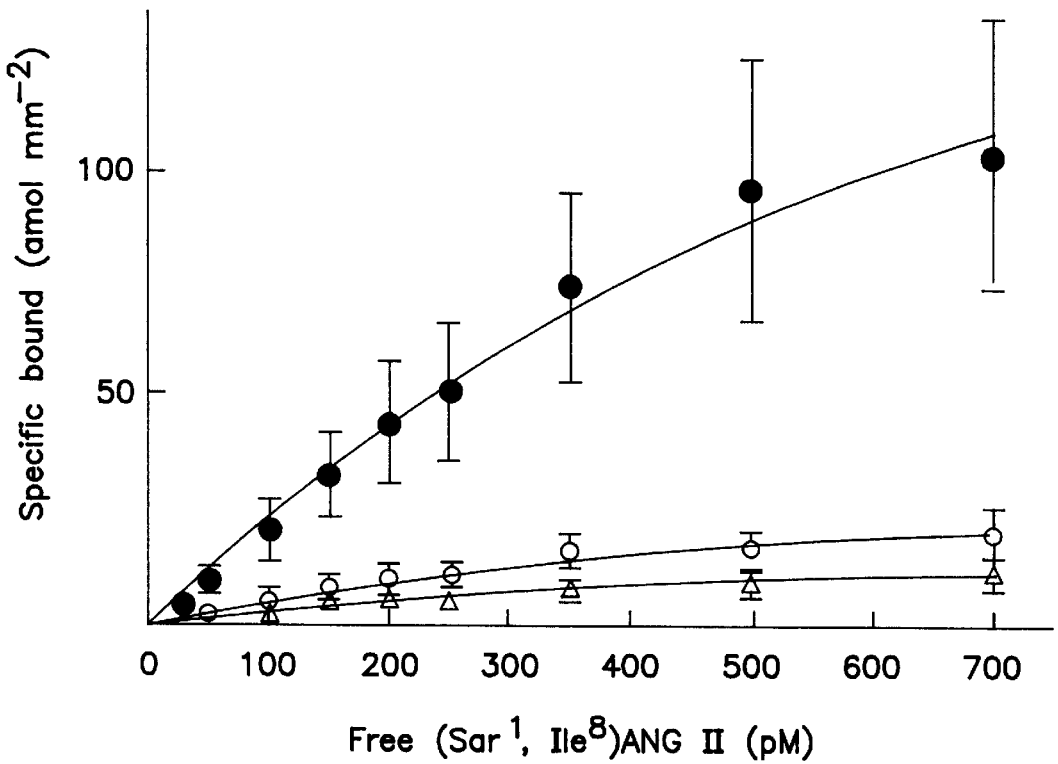

FIG. 1 Specific equilibrium binding of increasing concentrations of $[^{125}I]$ (Sar$^1$, Ile$^8$) angiotensin II to synovium from patients with osteoarthritis. Maximal binding was greater to blood vessels; than to lining cells (○) (p<0.001), and greater to lining cells than to stroma (Δ) (p<0.01). Data are means (±S.E.M.) of 6 cases.

Figure 2:
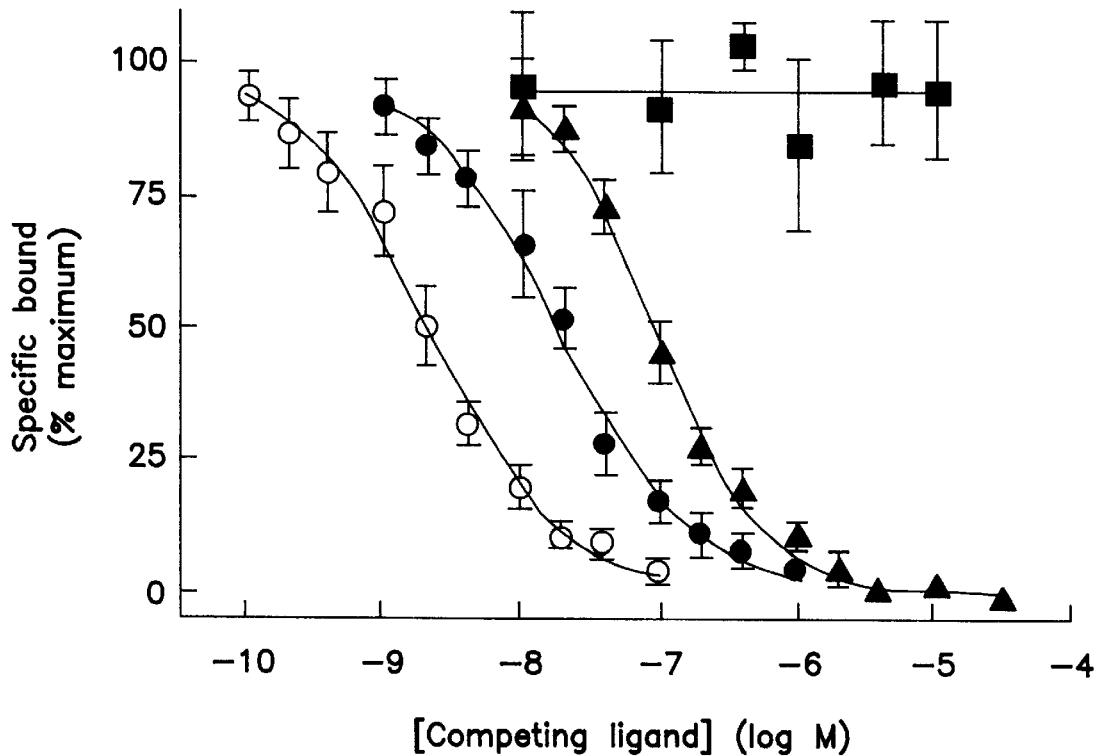

FIG. 2 Inhibition of specific binding of $[^{125}I]$ (Sar$^1$, Ile$^8$) angiotensin II to blood vessels in synovium from patients with osteoarthritis by unlabelled (Sar$^1$, Ile$^8$) angiotensin II (○), angiotensin II; the AT$_1$ specific antagonist (E)-3-[2-n-butyl-1-{4-carboxyphenyl)methyl}-1H-imidazol-5-yl]-2-(2-thienyl)methyl-2-propenoic acid (D) and the AT$_2$ specific antagonist PD123319 (o). Data are means (±S.E.M.) of 6 cases.

DESCRIPTION OF THE INVENTION

The present invention is a therapeutic method for treating chronic inflammatory conditions in a mammal, especially humans. The present invention has found that locally generated AII is present in human synovium and therefore use of AII receptor antagonists will contribute to the treatment of chronic inflammatory conditions. Preferably, the AII receptor antagonist is of the AT$_1$ receptor antagonist subtype.

The observation of the presence of Angiotensin II receptors on synovial cells gives rise to the speculation that this tissue which is reactive and proliferates in response to injury may reflect a broader role for angiotensin in the regulation of tissue injury, proliferation and differentiation. As such this would include treatment of disorders such as tumor growth, i.e. neoplastic transformation and growth/metasis, bone marrow maturation and differentiation, skin maturation and differentiation, and hepatocyte maturation and differentiation. Chronic inflammatory diseases would also include the proliferative lymphocyte responses, such as inflammatory auto immune diseases (preferably other than psoriasis and other topical skin disorders), systemic lupus erythrematous, rheumatoid arthritis and diabetes. Chronic inflammatory diseases also include the connective tissue disorders such as Sjogrens disease, multiple sclerosis, scloderma, and the mixed connective tissue disorders which include multiple organs, such as the kidney, thyroid and salivary glands. Chronic inflammatory diseases also include disorders such as inflamed joints, rheumatoid arthritis, rheumatoid spondylitis, and gouty arthritis and the various other arthritic conditions such as osteoarthritis and chondromalacia patellae. Chondromalacia, or destruction of cartilage is a characteristic present in inflammatory conditions of the joint. It is also recognized that while osteoarthritis is not considered an inflammatory condition, per se, it is included as an arthritic condition for the purposes herein.

Particularly preferred are disorders associated with synovial proliferation and response to injury in the joint, such as inflamed joints, rheumatoid arthritis, rheumatoid spondylitis, and gouty arthritis and the various other arthritic conditions such as osteoarthritis and chondromalacia patellae.

As will be discussed in the Methods section below, specific binding of $[^{125}I]$ (Sar$^1$, Ile$^8$)AII and ACE-like immunoreactivity was observed respectively in the media and endothelium of synovial arterioles, suggesting that these vessels may be subject to the actions of locally generated AII.

AT$_1$-like binding sites have previously been demonstrated in media of large and medium sized arteries in man (Urata et al. J. Clin., *Endocrinol. Metabl.*, Vol. 69, pp 54–66 (1989); and on cultured vascular smooth muscle cells (Whitebread et al., *Biochem. Biophys, Res. Commun., Vol.* 163, pp 264–291 (1989); and are believed to mediate vasoconstriction (Chiu et al., *J. Pharmacol. Exp Therapeut.*, Vol. 252 pp 711–718 (1990) and smooth muscle hypertrophy (Millet et al., *Eur. J. Biochem*, Vol. 206, pp 367–372, (1992), both of which may reduce tissue perfusion. Synovial hypoperfusion may contribute to the pathogenesis of human arthritis (Levick, J. R., *J. Rheumatol.*, Vol. 17, pp 579–582 (1990), and the potential of AT$_1$ antagonists to enhance tissue perfusion (Azuma et al., *Br. J. Pharmacol.*, Vol. 106, pp 665–671 (1992).

Open, uncontrolled studies of ACE inhibition in inflammatory arthritis have been inconclusive, providing some evidence that ACE inhibitor Captopril may be of therapeutic benefit (Martin et al., *Lancet*, i, pp 1325–1328 (1984), although such beneficial effects need not necessarily be attributable to the inhibition of ACE (Bird et al., *J. Rheumatol.*, Vol. 17, pp 603–608 (1990). Furthermore, angiotensinogen is not the only substrate for ACE, which also inactivates proinflammatory peptides such as bradykinin and substance P, both of which may be involved in arthritis (Miao et al., *Neuroscience*, Vol. 51, pp 649–655 (1992), Walsh et al. *Ann. Rheum. Dis.*, Vol. 51 pp 313–317 (1992), Caspritz et al. *Arzneimittelforschung*, Vol. 36, pp 1605–1608 (1986). Inhibition of ACE may therefore have multiple actions which may mask any beneficial effect of reducing AII generation.

The present invention provides a novel approach to the therapy of chronic inflammatory conditions, particularly of the joint, by use of the class of compounds referred to as angiotenstion receptor antagonists, and preferentially the class of compounds which inhibit the $AT_1$ subtype receptors and are referred to has $AT_1$ receptors antagonists. Preferably, for use herein the $AT_1$ receptors antagonists are losartan and (E)-3-[2-n-butyl-1-{4-carboxyphenyl)methyl}-1H-imidazol-5-yl]-2-(2-thienyl)methyl-2-propenoic acid.

AII acts via specific cell surface receptors, of which two subtypes have been defined pharmacologically. The human $AT_1$ subtype has been recently cloned (Furuta et al., *Biochem. Biophys. Res. Commun.*, Vol. 183, pp 8–13 (1992), Takayanagi et al., *Biochem. Biophys. Res. Commun.*, Vol. 183, pp 910–916 (1992), Bergsma et al., *Biochem. Biophys. Res. Commun.*, Vol. 183, pp 989–995 (1992), and is a member of the superfamily of G protein-coupled transmembrane receptors. $AT_1$ antagonists such as losartan (Whitebread et al., supra) and (E)-3-[2-n-butyl-1-{4-carboxyphenyl)methyl}-1H-imidazol-5-yl]-2-(2-thienyl)methyl-2-propenoic acid (Weinstock et al., *J. Med. Chem.*, Vol. 34, pp 1514–1517 (1991), sensitivity to reducing agents such as dithiothreitol (DTT) (Whitebread et al., supra) and to guanine nucleotides (Bottari et al., *Eur. J. Pharmacol.*, Vol. 207, pp 157–163 (1991). By contrast, $AT_2$ receptors are not inhibited by DTT, are not apparently G protein-coupled and are sensitive to specific $AT_2$ receptor antagonists such as PD123319 (Dudley et al., *Mol. Pharmacol.*, Vol. 40, pp 360–367 (1991).

One aspect of the present invention is the utilization of a class of antagonists which have been previously prepared and evaluated as effective AII receptor antagonists. Examples of suitable angiotensin II receptor antagonists include, but are not limited to, the following:

Imidazoles substituted in the 5-position by a 2-heteroaryl-2-propenoic acid group that are described in Finkelstein, et al., U.S. Pat. No. 5,185,351, issued Feb. 9, 1993 whose disclosure is incorporated herein by reference in its entirety.

Preferred compounds included within the scope of this patent are:

(E)-3-[2-n-butyl-1-{4-carboxyphenyl)methyl}-1H-imidazol-5-yl]-2-(2-thienyl)methyl-2-propenoic acid, (E)-3-[2-n-butyl-1-{4-carboxynaphth-1-yl)methyl}-1H-imidazol-5-yl]-2-(2-thienyl)methyl-2-propenoic acid, (E)-3-[2-n-butyl-1-{2-chloro-4-carboxyphenyl)-methyl}-1H-imidazol-5-yl]-2-(2-thienyl)methyl-2-propenoic acid, and (E)-3-[2-n-butyl-1-{4-carboxy-2,3-dichlorophenyl)-methyl}1H-imidazol-5-yl]-2-(2-thienyl)methyl-2-propenoic acid; or a pharmaceutically acceptable salt thereof.

Particularly preferred compounds are (E)-3-[2-n-butyl-1-{(4-carboxyphenyl)methyl}-1H-imidazol-5-yl]-2-(2-thienyl)methyl-2-propenoic acid and (E)-3-[2-n-butyl-1-{4-carboxynaphth-1-yl)methyl}-1H-imidazol-5-yl]-2-(2-thienyl)methyl-2-propenoic acid; or a pharmaceutically acceptable salt thereof.

The most preferred compound of this invention is (E)-3-[2-n-butyl-1-{(4-carboxyphenyl)methyl]-1H-imidazolyl-5-yl]-2-(2-thienyl)methyl-2-propenoic acid methanesulfonate.

Substituted (imidazolyl)alkenoic acids that are described in European Finkelstein, et al., Publication No. EP 0 403 158, published on Dec. 19, 1990 whose disclosure is incorporated herein by reference in its entirety.

Preferred compounds included within the scope of this class of AII receptor antagonists are:

(E)-3-[2-n-butyl-1-{(2-chlorophenyl)methyl}-1H-imidazol-5-yl]-2-(3,4-methylenedioxyphenyl)methyl-2-propenoic acid, (E)-3-[2-n-butyl-1-{(4-carboxyphenyl)methyl}-1H-imidazol-5-yl]-2-n-butyl-2-propenoic acid, and (E)-3-[2-n-butyl-1-{(4-carboxyphenyl)methyl}-1H-imidazol-5-yl]-2-n-benzyl-2-propenoic acid; or a pharmaceutically acceptable salt thereof.

Substituted 5-[(tetrazolyl)alkenyl]imidazoles that are described in Keenan et al., U.S. Pat. No. 5,177,091, issued Jan. 5, 1993 whose disclosure is incorporated herein by reference in its entirety.

Preferred compounds included within the scope of this class of AII receptor antagonists are:

(E)-1-[2-n-butyl-1-{(4-carboxyphenyl)methyl}-1H-imidazol-5-yl]-2-(1H-tetrazol-5-yl)-3-(2-thienyl)-1-propene and (E)-1-[2-n-butyl-1-{(4-(1H-tetrazol-5-yl)phenyl)-methyl}-1H-imidazol-5-yl]-2-(1H-tetrazol-5-yl)-3-(2-thienyl)-1-propene; or a pharmaceutically acceptable salt thereof.

Substituted N-(imidazolyl)alkyl alanine derivatives that are described in Girard, et al., in European Publication No. EP 0 427 463, published on May 15, 1991 whose disclosure is incorporated herein by reference in its entirety.

Preferred compounds included within the scope of this application are:

N-[{1-(4-carboxyphenyl)methyl]-2-n-butyl-1H-imidazol-5-yl}methyl]-β-(2-thienyl)alanine and N-[{1-(2-chlorophenyl)methyl]-2-n-butyl-1H-imidazol-5-yl}methyl]-β-(2-thienyl)alanine; or a pharmaceutically acceptable salt thereof.

Substituted 5-(alkyl)carboxamide imidazoles that are described in Finkelstein, et al., U.S. Pat. No. 5,234,917, issued Aug. 10, 1993 whose disclosure is incorporated herein by reference in its entirety.

Preferred compounds included within the scope of the class of AII receptor antagonist are N-[{2-n-butyl-1-(2-chlorophenyl)methyl-1H-imidazol-5-yl}methyl-carbonyl]-L-phenylalanine and N-[{2-n-butyl-1-(2-chlorophenyl)methyl-1H-imidazol-5-yl}methylcarbonyl]-L-(2-thienyl)alanine; or a pharmaceutically acceptable salt thereof.

Substituted histidines that are described in Gleason, et al., PCT Publication No. WO 92/00068, published Jan. 9, 1992 whose disclosure is incorporated herein by reference in its entirety.

Preferred compounds included within the scope of this application are 3-[(2-chlorophenyl)methyl]-2-propylthio-N-butrylhistidine and 3-[(2-chlorophenyl)-methyl]-2-n-butyl-N-butyrylhistidine; or a pharmaceutically acceptable salt thereof.

Substituted [1H-imidazol-5-yl]alkanoic acids that are described in Girard, et al., PCT Publication No. WO 92/02510, published Feb. 20, 1992 whose disclosure is incorporated herein by reference in its entirety.

A preferred compound included within the scope of this application is 3-[2-n-butyl-1-{(2-chlorophenyl)-methyl}-1H-imidazol-5-yl]-2-benzylpropanoic acid or a pharmaceutically acceptable salt thereof.

Substituted 5-aryl imidazoles that are described in Keenan, et al., PCT Publication No. WO 92/09278, published Jun. 11, 1992 whose disclosure is incorporated herein by reference in its entirety.

A preferred compound included within the scope of this application is 3-[2-n-butyl-1-{(2-chlorophenyl)-methyl}-1H-imidazol-5-yl]benzoic acid or a pharmaceutically acceptable salt thereof.

Substituted benzimidazoles that are described in Franz, et al., PCT Publication No. WO 91/16313, published Oct. 31, 1991 whose disclosure is incorporated herein by reference in its entirety.

A preferred compound included within the scope of this application is 2-n-butyl-1-(4-carboxyphenyl)methyl-5-chloro-1H-benzimidazole-7-carboxylic acid or a pharmaceutically acceptable salt thereof.

The following angiotensin II receptor antagonists are also included within the scope of the instant invention. Since it is contemplated that any AII receptor antagonist will possess the novel utility herein described, the list below is not a limitation on the scope of the present invention.

| AII Analog* | Reference Citing AII Receptor Blocking Activity |
|---|---|
| $Sar^1$ $Ala^8$ | Clin. Sci. 57: 71, 1979 |
| $Sar^{Sar}$ $Ile^8$ | Endocrinology 107(5): 1365, 1980 |
| $Succ^1$ $Val^5$ $Phenylgly^8$ | Clin. Sci. Mol. Med. 51: 4305, 1976 |
| $desAsp^1$ $Ile^8$ | Am. J. Physiol. 236(3): F252, 1976 |
| $Sar^1$ $Thr^8$ | Clin. Sci. Mol. Med. 51: 3855, 1976 |
| $Sar^1$ Cys—$Me^8$ | J. Cardiovasc. Pharm. 5: 1025, 1983 |
| $Sar^1$ Tyr—$Me^4$ | Life Sci. 34: 317, 1983 |
| $Gly^8$ | Can J. Physiol Pharm. 57: 121, 1979 |
| $Ile^8$ | Can J. Physiol Pharm. 57: 121, 1979 |
| $Leu^8$ | Can J. Physiol Pharm. 57: 121, 1979 |
| $Sar^1$ $Leu^8$ | Can J. Physiol Pharm. 57: 121, 1979 |
| $desAsp^1$ $Leu^8$ | Can J. Physiol Pharm. 57: 121, 1979 |
| $Sar^1$ Me—$Ala^7$ $Ile^8$ | Can J. Physiol Pharm. 57: 763, 1979 |
| $Sar^1$ DL-Nipecotamide$^7$ $Ile^8$ | Can J. Physiol Pharm. 57: 763, 1979 |
| $Sar^1$ $Sar^7$ $Ile^8$ | Can J. Physiol Pharm. 57: 763, 1979 |
| 8-L-Ala | J. Pharm. Pharmacol. 32: 232, 1980 |
| $Met^8$ | J. Med. Chem. 22(9): 1147, 1979 |
| $Thr^8$ | J. Med. Chem. 22(9): 1147, 1979 |
| O—Me $Thr^8$ | J. Med. Chem. 22(9): 1147, 1979 |
| N—Me $Ile^8$ | J. Med. Chem. 22(9): 1147, 1979 |
| N—Me $Phe^8$ | J. Med. Chem. 22(9): 1147, 1979 |
| $Sar^1$ $Sar^7$ $Leu^8$ | J. Med. Chem. 22(9): 1147, 1979 |
| $Sar^1$ $Sar^7$ $Thr(Me)^R$ | J. Med. Chem. 22(9): 1147, 1979 |
| $Sar^1$ $Sar^7$ $DLaIle^8$ | J. Med. Chem. 22(9): 1147, 1979 |
| $MeIle^1$ $Thr^8$ | J. Med. Chem. 20(2): 253, 1977 |
| $Me_2$ $Gly^1$ $Thr^8$ | J. Med. Chem. 20(2): 253, 1977 |
| $GdnAC^1$ $Thr^8$ | J. Med. Chem. 20(2): 253, 1977 |
| $desAsp^1$ $Thr^8$ | J. Med. Chem. 20(2): 253, 1977 |
| $Sar^1$ $Ser(Me)^8$ | J. Med. Chem. 20(2): 253, 1977 |
| $Sar^1$ $Thr^8$ | J. Med. Chem. 20(2): 253, 1977 |
| $Sar^1$ $Thr(Me)^8$ | J. Med. Chem. 19(2): 244, 1976 |
| $MeAspNH_2^1$ $Ile^8$ | J. Med. Chem. 19(2): 244, 1976 |
| $Sar^1$ $MeTyr^4$ $Ile^8$ | J. Med. Chem. 19(2): 244, 1976 |
| $Sar^1$ $MeIle^5$ $Ile^8$ | J. Med. Chem. 19(2): 244, 1976 |
| $Sar^1$ $MeIle^8$ | J. Med. Chem. 19(2): 244, 1976 |
| $Sar^1$ $MeIle^5$ $MeIle^8$ | J. Med. Chem. 19(2): 244, 1976 |
| $Sar^1$ Thr (O—/—Me)$^8$ | J. Med. Chem. 19(2): 244, 1976 |
| $Sar^1$ $Met^8$ | J. Med. Chem. 19(2): 244; 1976 |
| $Sar^1$ $Ser^8$ | J. Med. Chem. 19(2): 244, 1976 |
| $Ile^5$ $Ala^8$ | J. Med. Chem. 13: 181, 1970 |

-continued

| AII Analog* | Reference Citing AII Receptor Blocking Activity |
|---|---|
| $Ile^5$,8-(3-amino-4-phenyl)butyric acid | J. Med. Chem. 13: 181, 1970 |
| $Asn^1$ $Ala^8$ | Circ. Res. 29: 664, 1971 |
| $Sar^1$ $Cys(Me)^8$ | Circ. Res. 46: 720, 1980 |
| $Phe^4$ $Tyr^8$ | Proc. Nat Acad. Sci. 67:1624 1970 |
| $OctanoylLeu^8$ | J. Med. Chem. 20: 898, 1977 |
| $Cys^8$ | Cir. Res. 31: 862, 1972 |
| $Phe^4$ $Tyr^8$ | Cir. Res. 31: 862, 1972 |
| $desAsp^1$ $Phe^4$ $Tyr^8$ | Cir. Res. 31: 862, 1972 |
| para-fluoro$Phe^4$ | Cir. Res. 31: 862, 1972 |
| para-fluoro$Phe^8$ | Cir. Res. 31: 862, 1972 |

*Abbreviations indicate substitutions in the Angiotensin II sequence Asp—Arg—Val—Tyr—Ile—His—Pro—Phe [SEQ ID NO:1] with the location of the substitution identified by the superscript.

Other classes of AII receptor antagonists useful in the instant invention are disclosed in the following references whose disclosures are incorporated herein in their entirety.

Sipos et al., U.S. Pat. No. 3,751,404, issued Aug. 7, 1973. A particularly preferred compound in this class of AII receptor antagonists is Sar-Arg-Val-Tyr-Val-His-Pro-β-Ala-OH [SEQ ID NO:2] which is also referred to as Saralasin.

Regoli et al., U.S. Pat. No. 3,907,762, issued Sep. 23, 1975. Examples of suitable compounds within this class are Asp-Arg-Val-Tyr-Ile-His-Pro-Val-OH [SEQ ID NO:3] and Asp-Arg-Val-Tyr-Ile-His-Pro-α-amino-n-butyric acid [SEQ ID NO:4].

Nyeki et al., U.S. Pat. No. 4,388,304, issued Jun. 14, 1983. Compounds disclosed in this patent include Sar-Arg-Val-Tyr-Ile-His-Pro-Ile-methyl ester [SEQ ID NO:5] and hydroxyacetyl-Arg-Val-Tyr-Ile-His-Pro-Thr-methyl ester [SEQ ID NO:6]. The same or similar compounds are also disclosed in European Patent No. 34,259.

Sipos et al., U.S. Pat. No. 3,886,134 issued May 27, 1975. Examples of compounds of this class are Sar-Arg-Val-Tyr-Val-His-Pro-Ala-OH[SEQ ID NO:7], Ser-Arg-Val-Tyr-Val-His-Pro-Ala-OH [SEQ ID NO:8], and Asn-Arg-Val-Tyr-Val-His-Pro-D-Leu-OH.

Kisfaludy et al., U.S. Pat. No. 4,179,433, issued Dec. 18, 1979. Examples of this class of compounds include aminooxyacetyl-Arg-Val-Tyr-Ile-His-Pro-Leu-OH [SEQ ID NO:9] and D-α-aminooxypropionyl-Arg-Val-Tyr-Ile-His-Pro-Leu-OH [SEQ ID NO:10].

Hallinan et al., U.S. Pat. No. 4,204,991, issued May 27, 1980. See also West German Offenlegungschrift No. 2846200 (Chemical Abstracts, Vol. 91, Abstract No. 74989d).

Kisfaludy et al., U.S. Pat. No. 4,209,442, issued Jun. 24, 1980. Examples include hydroxyacetyl-Arg-Val-Tyr-Ile-His-Pro-Leu-OH [SEQ ID NO 11], hydroxyacetyl-Arg-Val-Tyr-Ile-His-Pro-Ala-OH [SEQ ID NO:12], and α-hydroxypropionyl-Arg-Val-Tyr-Ile-His-Pro-Ile-OH [SEQ ID NO:13].

Nyeki et al., U.S. Pat. No. 4,330,532, issued May 18, 1982. Exemplary compounds of this class are Sar-Arg-Val-Tyr-Ile-His-Pro-Lac [SEQ ID NO:14], Sar-Arg-Val-Tyr-Ile-His-Pro-Lac(OC$_2$H$_5$) [SEQ ID NO:15], and Sar-Arg-Val-Tyr-Ile-His-Pro-2-hydroxy-3-methylvaleric acid [SEQ ID NO:16].

Furukawa et al., U.S. Pat. No. 4,340,598 issued Jun. 20, 1982. Examples include 1-benzyl-4-chloro-2-phenylimidazole-5-acetamide, 1-benzyl-2-n-butyl-4-chloroimidazole-5-acetamide, and 1-benzyl-2-n-butyl-5-chloroimadazole-4-acetic acid.

Furukawa et al., U.S. Pat. No. 4,355,040, issued Oct. 19, 1982. Examples include 1-(2-chlorobenzyl)-2-n-butyl-4- chloroimidazole-5-acetic acid and 1-benzyl-4-chloro-2-(4-chloro-3,5-dinitrophenyl)imidazole-5-acetic acid.

Furukawa, et al., in European Patent Publication No. 103 647, published Mar. 28, 1984. A preferred compound included within the scope of this class of AII receptor antagonists is 4-chloro-1-(4-hydroxy-3-methylbenzyl)-2-phenylimidazole-5-acetic acid or a pharmaceutically acceptable salt thereof.

Carini et al., in European Patent Publication No. 253 310, published Jan. 20, 1988. Preferred compounds included within this class of AII receptor antagonists are 2-n-butyl-4-chloro-1-[(2'-(1H-tetrazol-5-yl)biphenyl-4-yl)methyl]-5-(hydroxymethyl)-imidazole and 2-n-butyl-4-chloro-1-[(2'-(carboxybiphenyl-4-yl)methyl]-5-(hydroxymethyl)-imidazole (also referred to as Losartan herein); or a pharmaceutically acceptable salt thereof.

Blankley et al., in European Patent Publication No. 245 637, published Nov. 19, 1987. Preferred compounds included within the scope of this class of AII receptor antagonists are 1-(2-phenylethyl)-5-phenylacetyl-4,5,6,7-tetrahydro-1H-imidazo[4,5-c]pyridine-6-carboxylic acid and 1-(4-amino-3-methylphenyl)methyl-5-diphenylacetyl-4,5,6,7-tetrahydro-1H-imidazo[4,5-c]pyridine-6-carboxylic acid; or a pharmaceutically acceptable salt thereof.

Carini et al., in European Patent Publication No. 323 841, published Jul. 12, 1989. Preferred compounds included in this class of AII receptor antagonists are 5-n-propyl-1-[(2'-carboxybiphenyl-4-yl)methyl]pyrrole-2-carboxylic acid, 3-methoxymethyl-5-n-propyl-4-[(2'-(1H-tetrazol-5-yl)biphenyl-4-yl)methyl]-1,2,4-triazole, and 3-methoxymethyl-5-n-butyl-1-[2'-carboxybiphenyl-4-yl)methyl]pyrazole; or a pharmaceutically acceptable salt thereof.

Carini, et al., U.S. Pat. No. 4,880,804, issued Nov. 14, 1989. Preferred compounds included within this class of AII receptor antagonists are 2-n-butyl-1-[(2'-carboxybiphenyl-4-yl)methyl]-5-hydroxymethylbenz-imidazole and 2-n-butyl-1-[(2'-carboxybiphenyl-4-yl)methyl]-6-hydroxymethylbenzimidazole; or a pharmaceutically acceptable salt thereof.

Carini, et al., U.S. Pat. No. 4,916,129, issued Apr. 10, 1990. A preferred compound included within this class of AII receptor antagonists is 5-[4-(3-(N-iso-propylamino)hydroxypropoxy)indole-2-carboxamidomethyl]-2-n-butyl-1-[(2'-carboxybiphenyl-4-yl)methyl]-4-chloroimidazole or a pharmaceutically acceptable salt thereof.

Rosenberg, et al., U.S. Pat. No. 4,857,507, issued Aug. 15, 1989. Examples include Boc-Phe-Leu amide of (4S)-3-oxo-4-amino-2,2-difluoro-1-isopropyl-mercapto-5-cyclohexylpentane and Boc-Phe-Leu amide of (3R,4S,EZ)-3-hydroxy-4-amino-2-fluoro-1-isopropyl-sulfonyl-5-cyclohexyl-1-pentene; or a pharmaceutically acceptable salt thereof.

Wissmann et al. U.S. Pat. No. 4,013,791, issued Mar. 22, 1977. An example of such compounds is succinamoyl-Arg-Val-Tyr-Val-His-Pro-Phegly-OH [SEQ ID NO:17] where Phegly-OH is a L-C-phenylglycine residue.

Bumpus et al., U.S. Pat. No. 3,923,769, issued Dec. 2, 1975.

Bumpus et al., U.S. Pat. No. 3,923,770, issued Dec. 2, 1975.

Bumpus et al. U.S. Pat. No. 3,923,771, issued Dec. 2, 1975.

Bumpus et al., U.S. Pat. No. 3,925,345, issued Dec. 9, 1975.

Bumpus et al., U.S. Pat. No. 3,976,770, issued Aug. 24, 1976.

Wille U.S. Pat. No. 3,915,948, issued Oct. 28, 1975. An example of an AII receptor antagonist included in this reference is Sar-Arg-Val-Tyr-Val-His-Pro-OH [SEQ ID NO:18].

Lifer, et al., European Patent Publication No. EP 0 438 869, published Jul. 31, 1991. A preferred compound of this class of AII receptor antagonists is α-hexyl-4-[(2-carboxy-3-hydroxybenzoyl)amino]-1H-imidazole-1-acetic acid ethyl ester or a pharmaceutically acceptable salt or solvate thereof.

Chakravarty, et al., European Patent Publication No. EP 0 401 030, published Dec. 5, 1990. A preferred compound of this class of AII receptor antagonists is 2-n-butyl-3-(2'-tetrazol-5-yl)biphenyl-4-yl)methyl-6,7-dihydroimidazo[4,5-e][1,4]diazepine-8(3H)-one or a pharmaceutically acceptable salt thereof.

Chakravarty, et al., European Patent Publication No. EP 0 400 974, published Dec. 5, 1990. An example included within the scope of this class of AII receptor antagonists is 5,7-dimethyl- 2-ethyl-3-(2'-(tetrazol-5-yl)biphenyl-4-yl) methyl-3H-imidazo[4,5-b]pyridine or a pharmaceutically acceptable salt thereof.

Chakravarty, et al., European Patent Publication No. EP 0 400 835, published Dec. 5, 1990. A preferred compound of this class of AII receptor antagonists is 4,6-dimethyl-2-ethyl-1-[2-(tetrazol-5-yl)biphenyl-4-yl]methylbenzimidazole or a pharmaceutically acceptable salt thereof.

Ashton, et al., European Patent Publication No. EP 0 409 332, published Jan. 23, 1991. A preferred compound of this class of AII receptor antagonists is 3-n-butyl-4-[4-(2-carboxybenzamido)benyl]-5-(2-methylbenzylthio)-4-1,2,4-triazole or a pharmaceutically acceptable salt thereof.

Greenlee, et al., European Patent Publication No. EP 0 407 102, published Jan. 9, 1991. A preferred compound of this class of AII receptor antagonists is 2-n-butyl-1,5-dihydro-4,5-dimethyl-1-[(2'-{1H-tetrazol-5-yl}{1,1-biphenyl}-4-yl)methyl]-pyrrolo[3,4-d]imidazole or a pharmaceutically acceptable salt thereof.

Carini, et al., European Patent Publication No. EP 0 324 377, published Jul. 19, 1989. A preferred compound of this class of AII receptor antagonists is 2-n-propyl-4-pentafluoroethyl-1-[2'-(1H-tetrazol-5-yl)biphenyl-4-yl)methyl]imidazole-5-carboxylic acid or a pharmaceutically acceptable salt thereof.

Oku, et al., European Patent Publication No. EP 0 3426 021, published May 8, 1991. A preferred compound of this class of AII receptor antagonists is 2-n-butyl-7-methyl-3-[(2-(1H-tetrazol-5-yl)biphenyl-4-yl]methyl]-3H-imidazo[4,5-b]pyridine or a pharmaceutically acceptable salt thereof.

Roberts, et al., European Patent Publication No. EP 0 412 848, published Feb. 13, 1991. A preferred compound of this class of AII receptor antagonists is 2-ethyl-4-(2'-(1H-tetrazol- 5-yl)biphenyl-4-yl)methoxy]quinoline or a pharmaceutically acceptable salt thereof.

Roberts, et al., Patent Cooperation Treaty Application Publication No. WO 91/07404, published May 30, 1991. A preferred compound of this class of AII receptor antagonists is 2-ethyl-4-[(2'-(1H-tetrazol-5-yl)biphenyl-4-yl)methoxy-1,5-naphthyridine or a pharmaceutically acceptable salt thereof.

Roberts, et al., European Patent Publication No. EP 0 399 732, published Nov. 28, 1990. A preferred compound of this class of AII receptor antagonists is 4-[(2-n-butyl-1H-benzimidazol-1-yl)methyl-N-phenylsulphonlybenzamide or a pharmaceutically acceptable salt thereof.

Miyake, et al., European Patent Publication No. EP 0 420 237, published Mar. 3, 1991. A preferred compound of this class of AII receptor antagonists is 7-methyl-2-n-propyl-3[-(2'(1H-tetrazol-5-yl)biphenyl-4-yl)methyl]-3H-imidazo[4,5-b] or a pharmaceutically acceptable salt thereof.

Narr, et al., European Patent Publication No. EP 0 392 317, published Nov. 17, 1990. Preferred compounds of this class of AII receptor antagonists are 4'-[(6-n-butanoylamino-2-n-butyl-benzimidazol-1-yl)methyl]biphenyl-2-carboxylic acid and 4'-[(2-n-butyl-6-cyclohexylamino-carbonyl)amino-benzimidazol-1-yl)methyl]biphenyl-2-carboxylic acid; or a pharmaceutically acceptable salt thereof.

Ross, et al., European Patent Publication No. EP 0 434 249, published Jun. 26, 1991, A preferred compound of this class of AII receptor antagonists is 1-{[3-bromo-2-[2-tetrazol-5-yl)phenyl]-5-benzofuranyl]methyl}-2-butyl-4-chloro-1H-imidazole-5-carboxylic acid or a pharmaceutically acceptable salt thereof.

Bernhart, et al., PCT Patent Publication No. WO 91/14679, published Oct. 3, 1991. A preferred compound of this class of AII receptor antagonists is 2-n-butyl-4-spirocyclopentyl-1-[(2'-(1H-tetrazol-5-yl)biphenyl-4-yl)methyl]-2-imidazolin-5-one or a pharmaceutically acceptable salt thereof.

Bühlmayer, et al., European Publication No. EP 0 443 983, published Aug. 28, 1991. A preferred compound of this class of AII receptor antagonists is (S)-N-(1-carboxy-2-methyl-prop-1-yl)-N-pentanoyl-N-[(2'-(1H-tetrazol-5-yl)biphenyl-4-yl)methyl]amine or a pharmaceutically acceptable salt thereof.

Naka, et al., European Publication No. 0 459 136, published Dec. 4, 1991. A preferred compound of this class of AII receptor antagonists is 1-(cyclohexyloxycarbonyloxy)-ethyl-2-ethoxy-1-[(2'-(1H-tetrazol-5-yl)biphenyl-4-yl)-methyl]benzimidazole-7-carboxylate or a pharmaceutically acceptable salt thereof.

The above descriptions of classes of AII antagonists for use in the present invention were taken from pending published patent applications, patents, publications and/or from abstracts thereof. Reference should be made to such patents and publications for their full disclosures of such classes and specific compounds within such classes, the entire disclosure of such patents and publications being incorporated herein by reference.

Many AII antagonists are known in the art and may be prepared by known methods or by variations thereof. Certain AII antagonists employed in the invention may exist in isomeric form. This invention includes all such isomers both in pure form and admixture, including racemic mixtures and their pharmaceutically acceptable salts.

Quantitative in vitro receptor audiography was used to localise and characterise receptors for angiotensin in human synovium in order to assess potential sites of action of locally generated AII and to assess whether specific angiotensin receptor antagonists can interact with angiotensin receptors in human synovium. The methods section herein describes the process used for such localisation.

The present invention has found that locally generated AII is present in human synovium, and that distinct synovial structures may bear different densities of $AT_1$ receptors rather than different receptor subtypes. Further, the present invention has found the lack of $AT_2$ receptors in such synovium. Therefore the use of $AT_1$ subtype AII receptor antagonists is preferred for use herein.

METHODS SECTION

A) Angiotensin II antagonist activity

Angiotensin II antagonist activity is assessed by in vitro methods In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. For the purposes of the present invention the preferred AII antagonists are compounds which are capable of inhibiting the action of AII by at least 50% at a concentration of 1 mM or less, and especially preferred AII antagonists are compounds which are capable of inhibiting the action of AII by at least 50% at a concentration of 25 nM or less when tested by the following standard methods.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. The $IC_{50}$ for (E)-3-[2-n-butyl-1-{4-carboxyphenyl)methyl}-1H-imidazol-5-yl]-2-(2-thienyl)methyl-2-propenoic acid is about 1.0 nM.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist dissociation constants ($K_B$) are calculated by the dose ratio method using the mean effective concentrations. The $K_B$ for (E)-3-[2-n-butyl-1-{4-carboxynaphth-1-yl)methyl}-1H-imidazol-5-yl]-2-(2-thienyl)methyl-2-propenoic acid is about 0.15 nM.

B) Receptor Autoradiography

Human tissues

Human knee synovium was collected at surgery from patients with osteoarthritis or rheumatoid arthritis undergoing total knee replacement and patients with chondromalacia patellae undergoing carbon fibre resurfacing of articular cartilage. Clinical details are given in table 1. Tissue samples were immediately embedded in Tissue-Tek (Miles Inc., Elkhart, Ind., USA) and frozen to cork mounts in melting isopentane without prior fixation. Specimens were stored at −40° C. until use. 10 μM thick sections were cut in a cryostat and thaw mounted onto Vectabond™ (Vector Laboratories, Peterborough, U.K.) treated slides, air dried and used immediately, or stored at −20° C. with silica gel for up to 5 days until use.

Ligand binding

Sections of rat knees were preincubated for 10 min in 10 mM phosphate buffered saline, pH 7.4, containing 5 mM $MgCl_2$, 5 mM ethylenediamine tetraacetic acid (EDTA) and 0.004% bacitracin (buffer A). Excess buffer was removed and sections were incubated for 90 minutes with ligand in buffer B (buffer A plus 1% bovine serum albumin). Ligand comprised 0.25 mM [$^{125}$I](Sar$^1$, Ile$^8$)AII or 0.25 mM [$^{125}$I]AII alone (total binding), or together with an excess (1 μM) of unlabelled (Sar$^1$, Ile$^8$)AII or AII respectively (non-specific binding). In experiments using [$^{125}$I]AII as ligand and those investigating the effect of guanosine 5'-O-(3-thiotriphosphate) (GTPγS) on inhibition of [$^{125}$I](Sar$^1$, Ile$^8$)

AII binding by AII, EDTA was omitted from both buffer A and B. Following incubation, sections were washed twice for 5 minutes at 4° C. in buffer A and rinsed in distilled water before being rapidly dried under a stream of cold air. Except where stated, incubations were performed at 22° C.

Quantification

Labelled sections were apposed to radiosensitive film (Hyperfilm-$^3$H, Amersham, UK) and exposed at 4° C. for 4 days ($[^{125}$I$](Sar^1, Ile^8)$AII) or 17 days ($[^{125}$I$]$AII). Films were developed in Kodak D9 for 3 minutes at 15° C. Autoradiographic images were analysed using an IBAS 386 image processing system. Synovial structures were identified, where necessary, by comparison of films with tissue sections counterstained with haematoxylin and eosin. Tissue structures (blood vessels, lining cells and regions of subintimal stroma displaying specific binding) were each delineated interactively. Binding was quantified on the 20 blood vessels in each section with the most dense specific binding. Binding density was derived from grey values by comparison with $^{125}$Iodine standards (Amersham, UK) co-exposed with each film, and corrected for the activity date of the ligand.

Microautoradiography

Tissue sections freshly labelled with $[^{125}$I$](Sar^1, Ile^8)$AII) were air dried then fixed in dry paraformaldehyde vapour for 30 minutes at 90° C. with silica gel dessicant. Sections were then dipped in radiosensitive emulsion (Ilford K5) at 42° C. and rapidly dried under a stream of cold air. Following exposure for 3 weeks at 4° C., emulsion-dipped slides were developed as for film autoradiograms, then counterstained with haematoxylin and eosin, dehydrated and mounted in dibutyl-pthalate polystyrene xylene(DPX, Raymond Lamb, London, UK). Preliminary experiments revealed that 'wet' fixation techniques in Bouin's fixative for 60 min did not prevent dissociation of specific binding during dipping. 'Dry' fixation in paraformaldehyde vapour for 30 min was considered optimal since shorter fixation times did not prevent dissociation of ligand, while longer fixation resulted in near total loss of haematoxylin and eosin reactivity.

Characterisation of binding sites

Specific binding was defined as total minus non-specific binding. Characterisation of specific binding was performed on samples of synovium from patients with osteoarthritis. The association rate of 0.25 nM $[^{125}$I$](Sar^1, Ile^8)$AII) to specific binding sites was assessed using incubation times from 5 to 300 minutes. Dissociation was measured as the decline in specific binding following incubation with 0.25 nM $[^{125}$I$](Sar^1, Ile^8)$AII for 90 minutes, then transfer of sections to an excess (400 ml) of buffer A without added ligand for 5 to 120 minutes.

Saturability of binding $K_d$ and $B_{max}$ values were measured by "hot" saturation studies with 25 to 700 pM $[^{125}$I$](Sar^1, Ile^8)$AII.

Specificity of binding was measured by binding inhibition studies using 0.25 nM $[^{125}$I$](Sar^1, Ile^8)$AII together with unlabelled ligands at concentrations between 100 pM and 10 $\mu$M, Inhibiting ligands included the agonist AII, the dual $AT_1/AT_2$ antagonist $(Sar^1, Ile^8)$AII, the selective $AT_1$ antagonists losartan and (E)-3-[2-n-butyl-1-{4-carboxyphenyl)methyl}-1H-imidazol-5-yl]-2-(2-thienyl) methyl-2-propenoic acid and the selective $AT_2$ antagonist PD123319. Sensitivity of specific binding to dithiothreitol (DTT) was assessed by incubation with 0.25 nM $[^{125}$I$](Sar^1, Ile^8)$AII together with 10 mM DTT. For comparison of receptor subtypes in synovia from patients with rheumatoid arthritis with those from patients with osteoarthritis, sections were incubated with 0.25 nM $[^{125}$I$](Sar^1, Ile^8)$AII alone (total binding), together with 1 $\mu$M unlabelled $(Sar^1, Ile^8)$AII (nonspecific binding, with 10 $\mu$M PD123319 ($AT_1$ receptors remain unblocked) or with 10 $\mu$M losartan ($AT_2$ receptors remain unblocked). Guanine nucleotide sensitivity of AII binding was assessed by coincubating sections with 0.25 nM $[^{125}$I$]$AII and 1 $\mu$M guanosine 5'-O-(3-thiotriphosphate (GTP$\gamma$S) and by measuring the inhibition of binding of 0.25 nM $[^{125}$I$](Sar^1, Ile^8)$AII by unlabelled AII in the presence and absence of 1 $\mu$M GTP$\gamma$S.

Statistical analysis

Kinetic and equilibrium constants were derived from specific binding values by iterative non-linear regression assuming single site models using GraphPAD Inplot4 (San Diego). Equilibrium binding densities ($B_{eq}$) were obtained with 0.25 nM $[^{125}$I$](Sar^1, Ile^8)$AII incubated for 90 minutes at 22° C. Values for binding inhibition constants ($K_i$) and HIll coefficients ($n_{Hill}$) were derived by fitting to sigmoid curves. Data from inhibition of $[^{125}$I$](Sar^1, Ile^8)$ binding by AII in the presence and absence of GTP$\gamma$S were fitted to one and two site models and the goodness of fit compared by F tests using GraphPAD Inplot4. Descriptive data are expressed as means (95% confidence interval) and between group comparisons were made using one way or repeated measures ANOVA and Student's t-test with Bonferroni correction on geometric data.

Immunohistochemistry

To further investigate the cellular localisation of specific $[^{125}$I$](Sar^1, Ile^8)$AII binding, and to compare the localisation of specific binding sites with that of angiotensin converting enzyme, consecutive sections to those used for emulsion-dipped preparations were immunostained using primary antibodies to endothelial, smooth muscle, macrophage, fibroblast and T cell markers (table 2). Cryosat sections (10 $\mu$M thick) were stained by the avidin-biotin complex (ABC) method of Hsu et al., 1981. In brief, sections were fixed in acetone for 5 minutes at 4° C., incubated with primary antibody for 2 hours at room temperature, then with biotinylated horse antimouse IgG or biotinylated goat antirabbit IgG for 1 hour, avidin-biotin complex for 30 minutes and finally developed in diaminobenzidine, dehydrated and mounted in DPX.

Materials $[^{125}$I$]Sar^1, Ile^8)$AII and $[^{125}$I$]$AII (specific activities each 2000 ci mmol$^{-1}$), $^{125}$Iodine standards, and Hyperfilm-$^3$H were obtained from Amersham International plc, Amersham, UK. Losartan was kindly provided by DuPont Merck, Wilmington, Del., U.S.A., (E)-3-[2-n-butyl-1-{4-carboxyphenyl)methyl}-1H-imidazol-5-yl]-2-(2-thienyl) methyl-2-propenoic acid by SmithKline Beecham, King of Prussia, Pa., U.S.A., and PD123319 by Parke-Davis, Ann Arbor, Mich., U.S.A. Other unlabelled peptides, guanine nucleotides, DTT, bacitracin and enzyme free bovine serum albumin were obtained from Sigma Chemical Co., Poole, UK. Biotinylated horse anti-mouse IgG and biotinylated goat anti-rabbit affinity purified IgG and avidin-biotin complex were from Vector Laboratories, Burlinggame, U.S.A.

RESULTS

Localisation $[^{125}$I$](Sar^1, Ile^8)$AII bound specifically and with high affinity to microvessels, lining cells and stromal cells in all cases. The distribution of binding is similar in chondromalacia patellae to that in rheumatoid arthritis. The distribution of binding observed with $[^{125}$I$](Sar^1, Ile^8)$ angiotensin II is identical to, but of lower density than that found on consecutive sections with $[^{125}$I$]$ angiotensin II. Nonspecific binding in consecutive sections of osteoarthritic synovium showed specific binding to the media of an arteriole. Consecutive sections of synovium from a patient with rheumatoid arthritis showed vascular binding of [$^{125}$I](Sar$^1$, Ile$^8$) angiotensin II. Binding to microvessels (<100 μM diameter) was more dense than to adjacent arteriolar media.

Specific binding of [$^{125}$I]AII had an identical distribution to that of [$^{125}$I] (Sar$^1$, Ile$^8$)AII, as demonstrated in consecutive sections, although specific [$^{125}$I]AII binding to each structure was only 15 to 22% as dense as the corresponding binding of (table 3). In synovium from all disease groups the densest binding of [$^{125}$I](Sar$^1$, Ile$^8$)AII was observed to synovial microvessels, with lining cells displaying less dense specific binding and binding to stromal cells being even less dense (table 4). In emulsion-dipped preparations, vascular binding of [$^{125}$I](Sar$^1$, Ile$^8$)AII was seen to comprise binding to arteriolar media (external diameter>100 μM) and to microvessels (external diameter<100 μM). Binding to microvessels appeared more dense than that to arteriolar media.

The localisation of [$^{125}$I](Sar$^1$, Ile$^8$)AII binding in emulsion-dipped preparations was compared with the distribution of different cell types in immunostaining of consecutive sections. Comparison with sections immunostained for the endothelial marker CD31 and the marker of vascular smooth muscle, α-smooth muscle actin confirmed that [$^{125}$I] (Sar$^1$, Ile$^8$)AII bound specifically to synovial arterioles and microvessels. Even the smallest microvessels identified by CD31 immunoreactive endothelia also displayed α-smooth muscle actin immunoreactivity, and it was not possible to resolve whether microvascular endothelium possessed specific [$^{125}$I](Sar$^1$, Ile$^8$)AII binding sites in addition to those on vascular smooth muscle. Immunostaining for angiotensin converting enzyme indicated a heterogenous distribution of ACE on synovial vascular endothelium, as described in Walsh et al., 1993, *Am. J. Pathol*, 142, pp 1610–1621 (1993) whose disclosure is incorporated by reference herein in its entirety. Arterioles and microvessels with intense endothelial ACE-like immunoreactivity also displayed specific [$^{125}$I](Sar$^1$, Ile$^8$)AII binding.

Immunostaining for the macrophage marker CD14 (FIG. 4) and the fibroblast marker 5B5 confirmed that regions of the synovial lining layer and stroma with specific [$^{125}$I] (Sar$^1$, Ile$^8$)AII binding contained both macrophage- and fibroblast-derived cells. It was not possible to resolve whether both or only one of these cell types displayed specific binding. Four samples of rheumatoid synovium contained follicular accumulations of lymphocytes, as demonstrated by immunoreactivity for the T cell marker OKT11. Specific [$^{125}$I](Sar$^1$, Ile$^8$)AII binding in these lymphoid follicles was restricted to CD31- and α-smooth muscle actin-positive blood vessels and to perifolicular connective tissue, rather than to T cells themselves. No differences in the localisation of specific [$^{125}$I](Sar$^1$, Ile$^8$)AII binding were observed between disease groups and equilibrium binding density to each synovial structure did not significantly differ between synovium from patients with chondromalacia patellae and that from patients with rheumatoid arthritis, nor, in separate experiments, between synovium from patients with osteoarthritis and that from patients with rheumatoid arthritis (table 4).

Characterisation

Specific binding of [$^{125}$I](Sar$^1$, Ile$^8$)AII to each synovial structure was time-dependent and reversible (table 5). Binding was staurable, with maximum binding densities greatest for synovial blood vessels and least for synovial stroma (table 5, FIG. 1). Binding to each structure was of high affinity, and no significant differences were found between structures in association and dissociation rates, nor in K$_d$ values (table 5).

Specific binding of [$^{125}$I](Sar$^1$, Ile$^8$)AII was inhibited by related compounds with a rank order of potencies (Sar$^1$, Ile$^8$)AII >AII>losartan=(E)-3-[2-n-butyl-1-{4-carboxyphenyl)methyl}-1H-imidazol-5-yl]-2-(2-thienyl) methyl-2-propenoic acid>PD123319 (table 5, FIG. 2). No significant differences in K$_i$ values were observed between structures. In synovium from patients with osteoarthritis and those with rheumatoid arthritis, specific ([$^{125}$I](Sar$^1$, Ile$^8$) AII binding to each structure was completely inhibited by the AT$_1$ antagonist losartan (10 μM), but was not significantly inhibited by the specific AT$_2$ antagonist PD123319 (10 μM) (table 6). Specific binding to each structure was completely inhibited by 10 mM DTT (table 7).

Binding of agonist ([$^{125}$I]AII to each structure was inhibited by the non-hydrolysable GTP analogue, GTPγS (1 μM), to levels not significantly different from nonspecific binding (data not shown). GTPγS (1 μM) did not inhibit ([$^{125}$I](Sar$^1$, Ile$^8$)AII binding. For each structure, inhibition of ([$^{125}$I] (Sar$^1$, Ile$^8$)AII binding by the agonist AII in the absence of EDTA and GTPγS was better described by a 2 site model than by a single site model (table 8) with 15 to 26% of the sites being of high affinity (IC$_{50}$ values<0.4 nM) and the remaining 74 to 85% of lower affinity (IC$_{50}$ values 7.0 nM). In the presence of 1 μM GTPγS, inhibition curves were described by a one site model corresponding to the lower affinity state (table 8) indicating abolition of the high affinity state by GTPγS.

Specific binding sites for [$^{125}$I](Sar$^1$, Ile$^8$)AII and [$^{125}$I] AII in human synovium have been demonstrated by the above noted methods. The identical distributions of binding and the inhibitory effect of GTPγS on agonist binding using either ligand, and inhibition of [$^{125}$I](Sar$^1$, Ile$^8$)AII binding by unlabelled AII suggest that both ligands label the same population of angiotensin receptors. The rank order of potencies for inhibition of specific binding, (Sar$^1$, Ile$^8$) AII>AII>losartan=(E)-3-[2-n-butyl-1-{4-carboxyphenyl) methyl}-1H-imidazol-5-yl]-2-(2-thienyl)methyl-2-propenoic acid>PD123319, inhibition of binding by DTT and of agonist binding by GTPγS are characteristic of the AT$_1$ subclass of angiotensin receptor (Whitebread et al., *Biochem. Biophys. Res. Commun.*, Vol. 163, pp 264–291 (1989); Weinstock et al., *J. Med. Chem.*, Vol. 34, 1514–1517 (1991). Binding studies performed in the presence of losartan or PD123319 provide no evidence for the presence of AT$_2$ receptors in synovium from any of these disease groups. The data indicates that distinct synovial structures bear different densities of AT$_1$ receptors rather than different receptor subtypes.

The most dense binding of [$^{125}$I](Sar$^1$, Ile$^8$)AII in human synovium was observed to synovial microvessels (<100 μM diameter). These microvessels also displayed endothelial ACE-like immunoreactivity. It was not possible to determine whether [$^{125}$I](Sar$^1$, Ile$^8$)AII bound to microvascular endothelium in addition to binding to smooth muscle cells, but specific binding of [$^{125}$I] AII has been previously demonstrated to each of these cell types in culture (Whitebread et al., 1989 suproa, Patel et al., *Am. J. Physiol.*, Vol. 256, C987–C993 (1989). Binding of angiotensins has previously been demonstrated to microvessels in brain (Proc. Natl. Acad. Sci. USA 1985:83;6340–3), retina (Farrari-Dileo et al., *Invest. Opthalmol. Vis. Sci.*, Vol. 32, pp 21–26 (1991) and kidney (Sechi et al., *Am. J. Physiol.*, Vol. 262, F236–F240 (1992). In addition to effects on vascular tone and smooth muscle growth, microvascular angiotensin receptors may regulate endothelial permeability (Morel et al., *Inflammation*, Vol. 14, pp 571–583 (1990) and neovascularisation (Fernandez et al., *J. Lab. Clin. Med.*, Vol. 105, pp 141–145 (1985); Le Noble et al., *Eur. H. Pharmacol.*, Vol. 195, pp 305–306 (1991).

Specifically, the results shown herein indicate that both AT1 receptor antagonists losartan and (E)-3-[2-n-butyl-1-{4-carboxyphenyl)methyl}-1H-imidazol-5-yl]-2-(2-thienyl) methyl-2-propenoic acid potently and completely inhibited binding of $[^{125}I](Sar^1, Ile^8)AII$ to microvessels, lining cells and stroma in inflamed human synovium.

Also demonstrated herein is the specific binding sites for $Sar^1$, $Ile^8$) and $[^{125}]AII$ to lining cells and stroma in human synovium, corresponding to the distribution of macrophages and fibroblasts. Both macrophages (Thomas and Hoffman, 1984 and fibroblasts (Millan et al. Science Vol., 244, pp 1340–1342, (1989) have previously been shown to express angiotensin receptors in culture. In vitro, angiotensin inhibits macrophage migration (Weinstock & Blum, *J. Immunol.*, Vol. 131, pp 2529–2532 (1983) and may increase phagocytosis (Weinstock & Kassab, *Cell. Immunol.*, pp 46–54 (1984), although the relevance of these observations to macrophage function in vivo remains uncertain.

Specific binding $[^{125}I](Sar^1, Ile^8)AII$ to adult human synovial stroma and lining cells was exclusively to $AT_1$-like sites, and was observed both in inflamed and uninflamed tissues. Therefore, chronic synovial inflammation is not associated with a switching from $AT_1$-receptors to $AT_2$-like receptors. Both losartan and (E)-3-[2-n-butyl-1-{4-carboxyphenyl)methyl}-1H-imidazol-5-yl]-2-(2-thienyl) methyl-2-propenoic acid, as shown herein, potently and completely inhibited binding of $[^{125}I](Sar^1, Ile^8)AII$ to microvessels, lining cells and stroma in inflamed human synovium thereby providing support for their use in the treatment of inflammatory arthritic conditions of the joint.

PHARMACEUTICAL FORMULATIONS

In the therapeutic use for the treatment of inflammatory joint disease, such as arthritis, the AII receptor antagonizing compounds of this invention are incorporated into standard pharmaceutical compositions. They can be administered orally, parenterally, rectally, topically or transdermally.

The compounds of the instant invention and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example, polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueious gums, celluloses, silicates or oils and the dispersion or suspension then filled into a soft gelatin capsule.

The compounds of the instant invention and their pharmaceutically acceptable salts which are active when administered parenterally (i.e. by injection of infusion) can be formulated as solutions or suspensions.

A composition for parenteral administration will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository composition comprises a compound of the instant invention or a pharmaceutically acceptable salt thereof which is active when administered in this way, with a binding and/or lubricating agent such as polymeric glycols, gelatins or coca butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

For topical administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

Preferably the composition is in unit dose form. Doses of the compounds of the instant invention in a pharmaceutical dosage unit will be an efficacious, non-toxic quantity selected from the range of 0.01–200 mg/kg of active compound, preferably 0.1–100 mg/kg. The selected dose is administered to a human patient in need of treatment of arthritis induced by angiotensin II from 1–6 times daily, orally, rectally, topically, by injection, or continuously by infusion. Oral dosage units for human administration preferably contain from 10 to 500 mg of active compound. Lower dosages are used generally for parenteral administration. Oral administration is used when safe, effective, and convenient for the patient.

No unacceptable toxicological effects are expected when compounds of the invention are administered in accordance with the present invention.

The following examples are intended to illustrate, but not to limit, the present invention.

TABLE 1

Details of cases used for comparative studies of synovial $[^{125}I]$ $(Sar^1, Ile^8)$ angiotensin II binding.

| Case | Age in years | Sex | Diagnosis | Duration (years) | [a]Current Medications |
|---|---|---|---|---|---|
| H93/368 | NA | NA | CMP | NA | NA |
| H93/369 | 56 | F | CMP | NA | nil |
| H93/245 | 45 | M | CMP | NA | NA |
| H93/353 | 22 | M | CMP | 0.5 | nil |
| H93/337 | 60 | M | CMP | 2 | nil |
| H93/228 | 41 | M | CMP | NA | NA |
| H93/293 | 38 | F | CMP | 6 | nil |
| H92/317 | 75 | F | OA | 13 | nil |
| H92/402 | 72 | F | OA | 10 | mefanamic acid |
| H92/819 | NA | M | OA | NA | NA |
| H92/849 | 71 | F | OA/CC | >4 | nil |
| 7/88(7) | 78 | F | OA | NA | NA |
| 10/87 | 59 | M | OA | 30 | nil |
| 183/89 | 59 | F | RA | 15 | SZ |
| 65/91 | 70 | F | RA | 17 | AZA, ENA, Ketoprofen |
| 216/89 | 65 | M | RA | NA | NA |

TABLE 1-continued

Details of cases used for comparative studies of synovial [$^{125}$I] (Sar$^1$, Ile$^8$) angiotensin II binding.

| Case | Age in years | Sex | Diagnosis | Duration (years) | [a]Current Medications |
|---|---|---|---|---|---|
| 12/87 | 60 | M | RA | 15 | Naproxen, Ibuprofen |
| 246/92 | 66 | F | RA | NA | MTX, Naproxen |
| H92/1940 | 67 | F | RA | 38 | Aspirin |
| H92/1992 | 39 | M | RA | 24 | MTX, Indomethacin |
| 174/89 | 66 | M | RA | 16 | nil |

Footnotes to table 1.
[a]Only slow acting antirheumatic agents, nonsteroidal antiinflammatory agents and angiotensin converting enzyme inhibitors are listed. No patient had received glucocorticosteroids within the month prior to surgery.
Abbreviations; AZA; azathioprine, CC; chondrocalcinosis, ENA; enalapril, MTX; methotrexate, QA; osteoarthritis, RA; rheumatoid arthritis, SZ; sulphasalazine.

Abbreviations; AZA; azathioprine, CC; chondrocalcinosis, ENA; enalapril, MTX; methotrexate, OA; osteoarthritis, RA; rheumatoid arthritis, SZ; sulphasalazine.

TABLE 2

Primary antibodies used for characterisation of structures displaying specific binding of [$^{125}$I] (Sar$^1$, Ile$^8$) angiotensin II.

| Cell Type | Antigen | Code | Clonality | Source | Ref. | Dilution |
|---|---|---|---|---|---|---|
| Endothelium | PECAM (CD31) | | Monoclonal | | | 1:1000 |
| Sooth Muscle | α-actin | IA4 | Monoclonal | Sigma | | 1:1000 |
| Macrophage | CD14 | UCHM 1 | Monoclonal | Sigma | Hogg et al. 1984 | 1:1000 |
| Fibroblast | prolyl-4-hydroxylase | 5B5 | Monoclonal | Dako | Hoyhty a et al., 1984 | 1:500 |
| T cell | CD2 | OKT11 | Monoclonal | Ortho | Verbi et al., 1982 | 1:1000 |

Abbreviations;

AJK; Dr A. J. Kenny, MRC Membrane Peptidase Group, Leeds, PECAM; platelet-endothelial cell adhesion molecule.

TABLE 3

Equilibrium binding of [$^{125}$I] angiotensin II binding and [$^{125}$I] (Sar$^1$, Ile$^8$) angiotensin II binding to structures in human synovium from 5 patients with osteoarthritis.

| Structure | Angiotensin II | (Sar$^1$, Ile$^8$) AII | Ratio (%) | p value |
|---|---|---|---|---|
| Blood vessel | 1.48 (0.77 to 2.86) | 6.83 (3.30 to 14.13) | 21.7 (9.8 to 48.2) | 0.006 |
| Lining Cell | 0.47 (0.18 to 1.23) | 3.18 (1.96 to 1.23) | 14.9 (6.3 to 35.3) | 0.004 |
| Stroma | 0.21 (0.12 to 0.37) | 0.98 (0.57 to 1.68) | 21.8 (7.6 to 62.3) | 0.02 |

(Sar$^1$, Ile$^8$)AII-(Sar$^1$, Ile$^8$) angiotensin II. Ratio=ratio of equilibrium binding of [$^{125}$I] angiotensin II to that of [$^{125}$I] (Sar$^1$, Ile$^8$) angiotensin II. Values are given in amol mm$^{-2}$ as geometric means (95% CI). Comparisons were made by Student's paired t test on geometric data.

TABLE 4

Equilibrium binding of [$^{125}$I]-labelled (Sar$^1$, Ile$^8$) angiotensin II binding to human synovium.

| | CMP (n = 6) | Osteoarthritis (n = 6) | Rheumatoid (n = 6) |
|---|---|---|---|
| Experiment I | | | |
| Blood vessels | — | [a]9.4 (4.2 to 20.9) | [a]9.2 (3.1 to 27.3) |
| Lining Cells | — | [b]3.6 (1.7 to 7.3) | [b]4.2 (1.8 to 9.9) |
| Stroma | — | 0.9 (0.2 to 3.1) | 1.3 (0.5 to 3.4) |
| Experiment II | | | |
| Blood vessels | [a]12.0 (6.4 to 22.7) | — | [a]16.3 (5.2 to 51.6) |
| Lining Cells | [b]4.4 (1.8 to 10.5) | — | [b]3.4 (0.7 to 16.2) |
| Stroma | 0.9 (0.2 to 3.4) | — | 0.7 (0.2 to 2.0) |

Experiments I and II were performed separately. No significant differences in specific binding densities were found in synovia from patients total knee replacement for osteoarthritis compared with those for rheumatoid arthritis (experiment I), nor in synovia from patients undergoing carbon fibre resurfacing for chondromalacia patellae (CMP) compared with synovia from patients undergoing total knee replacement for rheumatoid arthritis (experiment II) (Bonferroni corrected p values all >0.05). In each disease group, specific binding to blood vessels was more dense than that to lining cells (p values<0.001, paired t tests), and that to lining cells more dense than that to stroma (p values<0.01, paired t tests). Values are given in amol mm$^{-2}$ as geometric means (95% confidence interval).

TABLE 5

Characteristics of [$^{125}$I]-labelled (Sar$^1$, Ile$^8$) angiotensin II binding to human osteoarthritic Synovium.

| | Blood vessels | Lining cells | Stroma |
|---|---|---|---|
| $k_{obs}$ (s$^{-1}$ × 10$^{-4}$) | 0.7 (0.2 to 1.8) | 2.0 (1.2 to 3.3) | 1.2 (0.6 to 2.5) |
| $k_{-1}$ (s$^{-1}$ × 10$^{-4}$) | 1.6 (0.9 to 3.0) | 2.0 (1.1 to 3.6) | 2.2 (1.3 to 3.7) |
| $B_{max}$ (amol mm$^{-2}$) | [a]154 (69 to 344) | [b]26.9 (12.7 to 57.2) | 11.8 (5.1 to 27.1) |
| $K_d$ (nM) | 0.55 (0.34 to 0.89) | 0.40 (0.20 to 0.81) | 0.32 (0.20 to 0.51) |
| $K_i$ values(nM) | | | |
| (Sar$^1$, Ile$^8$) AII | [c]1.55 (0.69 to 2.95) | [c]1.38 (0.93 to 2.00) | [c]3.39 (2.19 to 5.25) |
| AII | [d]12.6 (6.6 to 24.6) | [d]8.32 (4.17 to 16.2) | [d]15.1 (7.41 to 31.6) |
| Losartan | [e]37.2 (15.9 to 87.1) | [e]102.3 (33.1 to 316.2) | [e]75.9 (32.4 to 177.8) |
| (E)-3-[2-n-butyl-1-{4-carboxyphenyl)-methyl}-1H-imidazol-5-yl]-2-(2-thienyl)methyl 2-propenoic acid | 49.0 (29.5 to 97.4) | 60.3 (25.1 to 144.5) | 81.3 (38.0 to 177.8) |
| PD 123319 | >10,000 | >10,000 | >10,000 |
| $n_{Hill}$ values | | | |
| (Sar$^1$, Ile$^8$) AII | 1.0 (0.8 to 1.3) | 1.2 (0.9 to 1.6) | 1.6 (1.2 to 2.0) |
| AII | 1.0 (0.6 to 1.5) | 0.9 (0.5 to 1.2) | 0.8 (0.5 to 1.2) |

TABLE 5-continued

Characteristics of [$^{125}$I]-labelled (Sar$^1$, Ile$^8$) angiotensin II binding to human osteoarthritic Synovium.

| | Blood vessels | Lining cells | Stroma |
|---|---|---|---|
| Losartan | 0.6 (0.4 to 0.8) | 0.9 (0.5 to 1.2) | 0.6 (0.3 to 0.8) |
| (E)-3-[2-n-butyl-1-{4-carboxyphen-yl)methyl}-1H-imidazol-5-yl]-2-(2-thienyl)methyl-2-propenoic acid | 1.2 (0.9 to 1.4) | 0.8 (0.6 to 1.0) | 0.8 (0.4 to 1.2) |
| PD 123319 | — | — | — |

Footnotes to Table 5:
[a] Maximal binding capacity ($B_{max}$) significantly greater to blood vessels than lining cells and than stroma (each p < 0.001) and
[b] significantly greater to lining cells than to stroma (p < 0.01, paired t tests). No significant differences observed between structures for other parameters. For each structures,
[c] (Sar$^1$, Ile$^8$) AII was significantly more potent than AII (each p < 0.05),
[d] AII was significantly more potent than losartan in lining cells (p < 0.05), and more potent than (E)-3-[2-n-butyl-)1-{4-carboxyphenyl)methyl}-1H-imidazol-5-yl[-2-(2-)thienyl)methyl-2-propenoic acid in all structures (each p < 0.05).
[e] no significant differences were observed in $K_i$ values between losartan and (E)-3-[2-n-butyl-1-(4-)carboxyphenyl)methyl}-1H-imidazol-5-yl]-2-(2-thienyl)methyl-2-)propenoic acid.

Values are expressed as geometric or arithmetic ($n_{Hill}$) means (95% confidence interval) and p values are corrected for multiple comparisons.

TABLE 6

Effect of the specific AT$_1$ antagonist Losartan and AT$_2$ antagonist PD 123319 on binding of [$^{125}$I] (Sar$^1$, Ile$^8$) angiotensin II binding to human synovium.

| | | Total | Nonspecific | Losartan | PD123319 |
|---|---|---|---|---|---|
| Blood Vessels | OA | 7.9 (6.0 to 10) | 2.4 (2.2 to 2.6) | [a]2.9 (2.4 to 3.5) | [b]7.1 (5.1 to 9.9) |
| | RA | 14 (5.6 to 36) | 2.6 (2.3 to 3.1) | [a]2.8 (2.3 to 3.3) | [b]12 (5.1 to 29) |
| Lining cells | OA | 3.6 (2.8 to 4.8) | 1.6 (1.4 to 1.8) | [a]1.7 (1.5 to 1.8) | [b]3.8 (2.9 to 4.4) |
| | RA | 5.7 (3.2 to 10) | 1.7 (1.6 to 1.9) | [a]1.8 (1.7 to 2.0) | [b]5.5 (3.5 to 8.7) |
| Stroma | OA | 2.4 (1.8 to 3.2) | 1.5 (1.4 to 1.6) | [a]1.5 (1.4 to 1.6) | [b]2.2 (1.8 to 2.6) |
| | RA | 3.0 (2.3 to 4.0) | 1.6 (1.5 to 1.7) | [a]1.5 (1.5 to 1.6) | [b]2.9 (2.1 to 4.1) |

TABLE 7

Inhibition by dithiothreitol (DTT) of [$^{125}$I] (Sar$^1$, ILe$^8$) angiotensin II binding to structures in synovium from patients with osteoarthritis.

| | Blood vessels | Lining cells | Stroma |
|---|---|---|---|
| Total | 10.2 (6.6 to 15.7) | 5.1 (3.3 to 7.9) | 2.6 (2.1 to 3.3) |
| Nonspecific | 3.2 (2.6 to 3.9) | 2.1 (1.8 to 2.3) | 1.7 (1.5 to 1.9) |
| + 10 mM DTT | [a]3.2 (2.9 to 3.5) | [a]2.0 (1.8 to 2.3) | [a]1.6 (1.5 to 1.7) |

Values are given in amol mm$^{-2}$ as geometric means (95% CI) and p values derived from paired t tests are corrected for multiple comparisons.

TABLE 8

Effect of 1 $\mu$M GTP$\gamma$S on inhibition of [$^{125}$I] (Sar$^1$, Ile$^8$) angiotensin II binding to osteoarthritic human synovium by unlabelled angiotensin II.

| | | IC$_{50}$ (nM) | | % | 1 vs. 2 site model | | |
|---|---|---|---|---|---|---|---|
| | | Site 1 | Site 2 | Site 1 | F | df | p |
| Blood vessels | –GTPgS | 7.0 (5.2 to 9.4) | .06 (.01 to .63) | 83 (76 to 91) | 13.9 | 5 | 0.009 |
| | +GTPgS | 11.5 (7.9 to 16.5) | — | — | 5.7 | 5 | 0.052 |
| Lining cells | –GTPgS | 9.1 (6.3 to 13.3) | .37 (0.6 to 3.5) | 85 (70 to 99) | 8.9 | 5 | 0.022 |
| | +GTPgS | 16 (12 to 21) | — | — | 1.5 | 5 | 0.309 |
| | –GTPgS | 8.6 (5.0 to 15.0) | .06 (.01 to .72) | 74 (62 to 85) | 11.6 | 5 | 0.013 |
| | +GTPgS | 20 (12 to 35) | — | — | 12 | 5 | 0.373 |

Best fitting curves representing mean data from synovia from 6 cases of osteoarthritis were generated according to a 2 site model when this gave a significantly better fit than a single site model, and otherwise according to a single site model. Estimates (95% CI) of IC$_{50}$ values and percent of sites in the lower affinity state (site 1) are given for the best fitting curves. In the absence of GTP$\gamma$S (–GTP$\gamma$S) the data for each structure are best fitted to 2 site models. In the presence of 1 $\mu$M GTP$\gamma$S single site models describe the data, with estimated IC$_{50}$ values corresponding to the lower affinity site observed in the absence of GTP$\gamma$S.

UTILITY EXAMPLES

I. METHODS

For the in vitro experiments, compounds were dissolved at appropriate concentrations in ethanol or DMSO (dimethylsulfoxide) having a final concentration of less than or equal to 1.0%, and then diluted to their respective concentrations using the buffers indicated in the text.

Unless otherwise noted, in the experiments herein where mice are used they are Balb/c mice obtained from Charles River Breeding Laboratories, and within a single experiment the mice were age-matched. Their weight range is from 21 to 30 g. The test groups generally contain 3–6 animals.

A) Adjuvant-induced arthritis in rats

Adjuvant-induced arthritis (AA) is produced in Lewis rats by a single intradermal injection of 0.75 mg of *Mycobacterium butyricum* in light paraffin oil, into the base of the tail. The adjuvant arthritis occurs after a delay of approximately 10 days and is characterized by inflammation of the hindpaws. In prophylatic studies, compounds are administered daily for 5 days, beginning on the sixth day after adjuvant injection. Hindpaw volumes were measured plethysmographically on days 14, 17 and 20.

$$\% \text{ inhibition} = \frac{\text{paw volume in arthritic control rats} - \text{paw volume in drug treated rats}}{\text{paw volume in arthritic control rats} - \text{paw volume in nonarthritic rats}} \times 100$$

Activity in adjuvant-induced arthritis, a complex model of immunologically-mediated inflammation, bone remodeling, and articular cartilage damage, suggests potential utility in a wide spectrum of arthritic and inflammatory diseases.

B) Arachidonic Acid-Induced Mouse Ear Inflammation

Arachidonic acid in acetone (2 mg/20 ml) is applied to the inner surface of the left ear. The thickness of both ears is then measured with a dial micrometer one hour after treatment, and the data is expressed as the change in thickness ($10^{-3}$ cm) between treated and untreated ears.

Test compounds are given orally in acid/saline at the times indicated prior to the topical application of arachidonic acid.

C) TPA-Induced Mouse Ear Edema

The administration of 12-0-tetradecanoylphobol acetate (TPA) to mouse ears has been shown to elicit inflammation that was attributed to both lipoxygenase (LO) and cyclooxygenase (CO) products.

TPA-Induced Inflammation:

TPA (12-0-tetradecanoylphobol acetate) (Sigma Chemical Co.) in acetone (4 µg/20 µl) is applied to the inner and outer surfaces of the left ear of BALB/c male mice. The thickness of both ears is then measured with a dial micrometer (Mitutoyo, Japan) at both 2 and 4 hours after treatment, and the data expressed as the change in thickness ($10^{-3}$ cm) between treated and untreated ears. The application of acetone does not cause an edematous response; therefore, the difference in ear thickness represented the response to TPA. After measuring the edema, the inflamed left ears are removed and stored at $-70°$ C. until they are assayed for MPO (myeloperoxidase) activity.

The test compounds are orally administered 15 minutes before application of the TPA. The results are the mean ± standard deviation from measurements on the 8 mice/group.

Assay of Myeloperoxidase (MPO) In Inflamed Ear Tissue:

On the day of the assay, partially thawed ear tissues are minced and then homogenized (10% w/v) with a Tissumizer homogenizer (Tekmar Co.) in 50 mM phosphage buffer (pH 6) containing 0.5% HTAB. The tissue homogenates are taken through three cycles of freeze-thaw, followed by brief sonication (10 sec.).

The method of Bradely et al., *J. Invest. Derm.*, 78:206, 1982, is used with the modifications described herein. The appearance of a colored product from the MPO-dependent reaction of o-dianisdine (0.167 mg/ml; Sigma Chemical Co.) and hydrogen peroxide (0.0005%; Sigma Chemical Co.) was measured spectrophotometrically at 460 nm. Supernatant MPO activity is quantified kinetically (change in absorbance measured over 3 min, sampled at 15 sec intervals) using a Beckman DU-7 spectrophotometer and a Kinetics Analysis package (Beckman Instruments, Inc.). One unit of MPO activity is defined as that degrading one micromole of peroxide per minute at 25° C.

D) Collagen-Induced Arthritis

Type II collagen arthritis is induced in male DBA/1 LacJ mice and bovine type II collagen is solublized in 0.01N acetic acid at a concentration of 2 mg/ml and emulsified with an equal volume of Freund's complete adjuvant (FCA). The emulsion is administered in accordance with the description and assay described in Griswold et al., Arthritis and Rheumatism, Vol. 31, No. 11, pp 1406–1412 (1988) whose disclosure is incorporated herein by reference in its entirety.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating chronic inflammatory diseases in a mammal in need thereof which comprises administering to said mammal an effective amount of an angiotensin II receptor antagonist selected from:

(E)-3-[2-n-Butyl-1-{4-carboxyphenyl)-methyl}-1H-imidazol-5-yl]-2-(2-thienyl)methyl-2-propenoic acid, or a pharmaceutically acceptable salt thereof;

(E)-3-[2-n-Butyl-1-{4-carboxynaphth-1-yl)methyl}-1H-imidazol-5-yl]-2-(2-thienyl)methyl-2-propenoic acid, or a pharmaceutically acceptable salt thereof;

2-n-Butyl-4-chloro-1-[(2'-(1H-tetrazol-5-yl)biphenyl-4-yl)methyl]-5-(hydroxymethyl)-imidazole, or a pharmaceutically acceptable salt thereof;

2-n-Propyl-4-pentafluoroethyl-1-[2'-(1H-tetrazol-5-yl)biphenyl-4-yl)methyl]imidazole-5-carboxylic acid, or a pharmaceutically acceptable salt thereof;

5,7-Dimethyl-2-ethyl-3-(2'-(tetrazol-5-yl)biphenyl-4-yl)methyl-3H-imidazo[4,5-b]pyridine;

2-Ethyl-4-{(2'-(1H-tetrazol-5-yl)biphenyl-4-yl)methoxy]quinoline, or a pharmaceutically acceptable salt thereof;

{[3-Bromo-2-[2-tetrazol-5-yl)phenyl]-5-benzofuranyl]methyl}-2-butyl-4-chloro-1H-imidazole-5-carboxylic acid, or a pharmaceutically acceptable salt thereof;

2-n-Butyl-4-spirocyclopentyl-1-[(2'-(1H-tetrazol-5-yl)biphenyl-4-yl)methyl]-2-imidazolin-5-one, or a pharmaceutically acceptable salt thereof;

(S)-N-(1-carboxy-2-methyl-prop-1-yl)-N-pentanoyl-N-[(2'-(1H-tetrazol-5-yl)biphenyl-4-yl)methyl]amine, or a pharmaceutically acceptable salt thereof;

4'-[(2-n-Butyl-6-cylcohexylamino-carbonyl)amino-benzimidazol-1-yl)methyl]biphenyl-2-carboxylic acid, or a pharmaceutically acceptable salt thereof; or 1-(Cyclohexyloxycarbonyloxy)ethyl-2-ethoxy-1-[(2'-(1H-tetrazol-5-yl)biphenyl-4-yl)methyl]-benzimidazole-7-carboxylate.

2. The method according to claim 1 wherein the angiotensin II receptor antagonist is (E)-3-[2-n-Butyl-1-{4-carboxyphenyl)-methyl}-1H-imidazol-5-yl]-2-(2-thienyl) methyl-2-propenoic acid or a pharmaceutically acceptable salt thereof.

3. The method according to claim 2 wherein the pharmaceutically acceptable salt is methanesulfonate.

4. The method according to claim 1 wherein the angiotensin II receptor antagonist is (E)-3-[2-n-Butyl-1-{4-carboxynaphth-1-yl)methyl}-1H-imidazol-5-yl]-2-(2-thienyl)methyl-2-propenoic acid or a pharmaceutically acceptable salt thereof.

5. The method according to claim 1 wherein the angiotensin II receptor antagonist is 2-n-Butyl-4-chloro-1-[(2'-(1H-tetrazol-5-yl)biphenyl-4-yl)methyl]-5-(hydroxymethyl)-imidazole or a pharmaceutically acceptable salt thereof.

6. The method according to claim 1 wherein the chronic inflammatory disease is arthritis.

7. The method according to claim 6 wherein the arthritis is rheumatoid arthritis, rheumatoid spondylitis, osteoarthritis, and gouty arthritis or is chondromalacia patellae.

8. The method according to claim 1 wherein the chronic inflammatory disease is a systemic autoimmune disease, or a connective tissue disorder.

9. The method according to claim 8 wherein the systemic autoimmune disease is selected from systemic lupus erythermatous, rheumatoid arthritis, diabetes; and the connective tissue disorder is selected from Sjogrens disease, multiple sclerosis, scloderma or is a mixed connective tissue disorder.

10. The method according to claim 6 wherein the angiotensin II receptor antagonist is (E)-3-[2-n-Butyl-1-{4-carboxyphenyl)-methyl}-1H-imidazol-5-yl]-2-(2-thienyl)methyl-2-propenoic acid, or a pharmaceutically acceptable salt thereof;

(E)-3-[2-n-Butyl-1-{4-carboxynaphth-1-yl)methyl}-1H-imidazol-5-yl]-2-(2-thienyl)methyl-2-propenoic acid, or a pharmaceutically acceptable salt thereof;

2-n-Butyl-4-chloro-1-[(2'-(1H-tetrazol-5-yl)biphenyl-4-yl) methyl]-5-(hydroxymethyl)imidazole, or a pharmaceutically acceptable salt thereof; or 2-n-Propyl-4-pentafluoroethyl-1-[2'-(1H-tetrazol-5-yl) biphenyl-4-yl)methyl]imidazole-5-carboxylic acid, or a pharmaceutically acceptable salt thereof.

11. The method according to claim 8 wherein the angiotensin II receptor antagonist is (E)-3-[2-n-Butyl-1-{4-carboxyphenyl)-methyl}-1H-imidazol-5-yl]-2-(2-thienyl)methyl-2-propenoic acid, or a pharmaceutically acceptable salt thereof;

(E)-3-[2-n-Butyl-1-{4-carboxynaphth-1-yl)methyl}-1H-imidazol-5-yl]-2-(2-thienyl)methyl-2-propenoic acid, or a pharmaceutically acceptable salt thereof;

2-n-Butyl-4-chloro-1-[(2'-(1H-tetrazol-5-yl)biphenyl-4-yl) methyl]-5-(hydroxymethyl)-imidazole, or a pharmaceutically acceptable salt thereof; or 2-n-Propyl-4-pentafluoroethyl-1-[2'-(1H-tetrazol-5-yl) biphenyl-4-yl)methyl]imidazole-5-carboxylic acid, or a pharmaceutically acceptable salt thereof.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:1:

Asp  Arg  Val  Tyr  Ile  His  Pro  Phe
    1                          5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide -continued ( i x ) FEATURE:
    ( A ) NAME/KEY: Modified-site
    ( B ) LOCATION: 1..2
    ( D ) OTHER INFORMATION: /product="MeGly"

( x i ) SEQUENCE DESCRIPTION: SEQ ID NO:2:

Xaa Arg Val Tyr Val His Pro Ala
1                       5

( 2 ) INFORMATION FOR SEQ ID NO:3:

( i ) SEQUENCE CHARACTERISTICS:
    ( A ) LENGTH: 8 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:3:

Asp Arg Val Tyr Ile His Pro Val
1                       5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Inhibitory-site
    ( B ) LOCATION: 7..8
    ( D ) OTHER INFORMATION: /product="Abu"

( x i ) SEQUENCE DESCRIPTION: SEQ ID NO:4:

Asp Arg Val Tyr Ile His Pro Xaa
1                       5

( 2 ) INFORMATION FOR SEQ ID NO:5:

( i ) SEQUENCE CHARACTERISTICS:
    ( A ) LENGTH: 8 amino acids
    ( B ) TYPE: amino acid
    ( C ) STRANDEDNESS: Not Relevant
    ( D ) TOPOLOGY: linear ( i i ) MOLECULE TYPE: peptide ( i x ) FEATURE:
    ( A ) NAME/KEY: Inhibitory-site
    ( B ) LOCATION: 7..8
    ( D ) OTHER INFORMATION: /product="other"
        / note= "methylester of Ile"

( i x ) FEATURE:
    ( A ) NAME/KEY: Modified-site
    ( B ) LOCATION: 1..2
    ( D ) OTHER INFORMATION: /product="MeGly"

( x i ) SEQUENCE DESCRIPTION: SEQ ID NO:5:

Xaa Arg Val Tyr Ile His Pro Ile
1                       5

( 2 ) INFORMATION FOR SEQ ID NO:6:

( i ) SEQUENCE CHARACTERISTICS:
    ( A ) LENGTH: 7 amino acids
    ( B ) TYPE: amino acid (C) STRANDEDNESS: Not Relevant
(D) TOPOLOGY: linear (ii) MOLECULE TYPE: peptide (ix) FEATURE:
    (A) NAME/KEY: Inhibitory-site
    (B) LOCATION: 1..2
    (D) OTHER INFORMATION: /product="other"
    /note= "hydroxyacetal of Arg"

(ix) FEATURE:
    (A) NAME/KEY: Inhibitory-site
    (B) LOCATION: 6..7
    (D) OTHER INFORMATION: /product="other"
    /note= "methyl ester of Thr"

(xi) SEQUENCE DESCRIPTION: SEQ ID NO:6:

Arg Val Tyr Ile His Pro Thr
1                        5

(2) INFORMATION FOR SEQ ID NO:7:

(i) SEQUENCE CHARACTERISTICS:
    (A) LENGTH: 8 amino acids
    (B) TYPE: amino acid
    (C) STRANDEDNESS: Not Relevant
    (D) TOPOLOGY: linear (ii) MOLECULE TYPE: peptide (ix) FEATURE:
    (A) NAME/KEY: Modified-site
    (B) LOCATION: 1..2
    (D) OTHER INFORMATION: /product="MeGly"

(xi) SEQUENCE DESCRIPTION: SEQ ID NO:7:

Xaa Arg Val Tyr Val His Pro Ala
1                        5

(2) INFORMATION FOR SEQ ID NO:8:

(i) SEQUENCE CHARACTERISTICS:
    (A) LENGTH: 8 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:8:

Ser Arg Val Tyr Val His Pro Ala
1                        5

(2) INFORMATION FOR SEQ ID NO:9:

(i) SEQUENCE CHARACTERISTICS:
    (A) LENGTH: 7 amino acids
    (B) TYPE: amino acid
    (C) STRANDEDNESS: Not Relevant
    (D) TOPOLOGY: linear (ii) MOLECULE TYPE: peptide (ix) FEATURE:
    (A) NAME/KEY: Inhibitory-site
    (B) LOCATION: 1..2
    (D) OTHER INFORMATION: /product="other"
    /note= "aminoocyacetyl deriv of arg"

(xi) SEQUENCE DESCRIPTION: SEQ ID NO:9:

Arg Val Tyr Ile His Pro Leu
1                        5

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Inhibitory-site
        ( B ) LOCATION: 1..2
        ( D ) OTHER INFORMATION: /product="other"
            / note= "aminooxypropionyl deriv of arg"

( x i ) SEQUENCE DESCRIPTION: SEQ ID NO:10:

Arg Val Tyr Ile His Pro Leu
1               5

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Inhibitory-site
        ( B ) LOCATION: 1..2
        ( D ) OTHER INFORMATION: /product="other"
            / note= "hydroxyacetal deriv of arg"

( x i ) SEQUENCE DESCRIPTION: SEQ ID NO:11:

Arg Val Tyr Ile His Pro Leu
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Inhibitory-site
        ( B ) LOCATION: 1..2
        ( D ) OTHER INFORMATION: /product="other"
            / note= "hydroxyacetal deriv of arg"

( x i ) SEQUENCE DESCRIPTION: SEQ ID NO:12:

Arg Val Tyr Ile His Pro Ala
1               5

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Inhibitory-site ( B ) LOCATION: 1..2
                ( D ) OTHER INFORMATION: /product="other"
                        / note= "alpha hydroxypropionyl deriv of arg"

( x i ) SEQUENCE DESCRIPTION: SEQ ID NO:13:

Arg  Val  Tyr  Ile  His  Pro  Ile
        1                   5

( 2 ) INFORMATION FOR SEQ ID NO:14:

( i ) SEQUENCE CHARACTERISTICS:
                ( A ) LENGTH: 7 amino acids
                ( B ) TYPE: amino acid
                ( C ) STRANDEDNESS: Not Relevant
                ( D ) TOPOLOGY: linear ( i i ) MOLECULE TYPE: peptide ( i x ) FEATURE:
                ( A ) NAME/KEY: Modified-site
                ( B ) LOCATION: 1..2
                ( D ) OTHER INFORMATION: /product="MeGly"

( i x ) FEATURE:
                ( A ) NAME/KEY: Inhibitory-site
                ( B ) LOCATION: 6..7
                ( D ) OTHER INFORMATION: /product="other"
                        / note= "lactic acid on pro"

( x i ) SEQUENCE DESCRIPTION: SEQ ID NO:14:

Xaa  Arg  Val  Tyr  Ile  His  Pro
        1                   5

( 2 ) INFORMATION FOR SEQ ID NO:15:

( i ) SEQUENCE CHARACTERISTICS:
                ( A ) LENGTH: 7 amino acids
                ( B ) TYPE: amino acid
                ( C ) STRANDEDNESS: Not Relevant
                ( D ) TOPOLOGY: linear ( i i ) MOLECULE TYPE: peptide ( i x ) FEATURE:
                ( A ) NAME/KEY: Modified-site
                ( B ) LOCATION: 1..2
                ( D ) OTHER INFORMATION: /product="MeGly"

( i x ) FEATURE:
                ( A ) NAME/KEY: Inhibitory-site
                ( B ) LOCATION: 6..7
                ( D ) OTHER INFORMATION: /product="other"
                        / note= "ethoxy deriv of lactic acid on pro"

( x i ) SEQUENCE DESCRIPTION: SEQ ID NO:15:

Xaa  Arg  Val  Tyr  Ile  His  Pro
        1                   5

( 2 ) INFORMATION FOR SEQ ID NO:16:

( i ) SEQUENCE CHARACTERISTICS:
                ( A ) LENGTH: 7 amino acids
                ( B ) TYPE: amino acid
                ( C ) STRANDEDNESS: Not Relevant
                ( D ) TOPOLOGY: linear ( i i ) MOLECULE TYPE: peptide ( i x ) FEATURE:
                ( A ) NAME/KEY: Modified-site
                ( B ) LOCATION: 1..2
                ( D ) OTHER INFORMATION: /product="MeGly"

( i x ) FEATURE:

(A) NAME/KEY: Inhibitory-site
                (B) LOCATION: 6..7
                (D) OTHER INFORMATION: /product="other"
                    / note= "2-hydroxy-3-methylvaleric acid on pro residue"

(xi) SEQUENCE DESCRIPTION: SEQ ID NO:16:

Xaa  Arg  Val  Tyr  Ile  His  Pro
    1                   5

(2) INFORMATION FOR SEQ ID NO:17:

(i) SEQUENCE CHARACTERISTICS:
                (A) LENGTH: 7 amino acids
                (B) TYPE: amino acid
                (C) STRANDEDNESS: Not Relevant
                (D) TOPOLOGY: linear (ii) MOLECULE TYPE: peptide (ix) FEATURE:
                (A) NAME/KEY: Inhibitory-site
                (B) LOCATION: 1..2
                (D) OTHER INFORMATION: /product="other"
                    / note= "succinamoyl deriv of arg"

(ix) FEATURE:
                (A) NAME/KEY: Modified-site
                (B) LOCATION: 6..7
                (D) OTHER INFORMATION: /product="OTHER"
                    / note= "xaa is phenylglycine"

(xi) SEQUENCE DESCRIPTION: SEQ ID NO:17:

Arg  Val  Thr  Val  His  Pro  Xaa
    1                   5

(2) INFORMATION FOR SEQ ID NO:18:

(i) SEQUENCE CHARACTERISTICS:
                (A) LENGTH: 7 amino acids
                (B) TYPE: amino acid
                (C) STRANDEDNESS: Not Relevant
                (D) TOPOLOGY: linear (ii) MOLECULE TYPE: peptide (ix) FEATURE:
                (A) NAME/KEY: Modified-site
                (B) LOCATION: 1..2
                (D) OTHER INFORMATION: /product="MeGly"

(xi) SEQUENCE DESCRIPTION: SEQ ID NO:18:

Xaa  Arg  Val  Tyr  Val  His  Pro
    1                   5